United States Patent
Johnson

(10) Patent No.: US 9,603,785 B2
(45) Date of Patent: Mar. 28, 2017

(54) SUNSCREEN/INSECT REPELLANT COMPOSITIONS AND METHODS OF MAKING AND USING THE SAME

(71) Applicant: Jerry Steven Johnson, Thomasville, GA (US)

(72) Inventor: Jerry Steven Johnson, Thomasville, GA (US)

(73) Assignee: Sunsect, Inc., Tallahassee, FL (US)

( * ) Notice: Subject to any disclaimer, the term of this patent is extended or adjusted under 35 U.S.C. 154(b) by 0 days.

(21) Appl. No.: 14/816,368

(22) Filed: Aug. 3, 2015

(65) Prior Publication Data

US 2016/0030316 A1 Feb. 4, 2016

Related U.S. Application Data

(60) Provisional application No. 62/031,992, filed on Aug. 1, 2014, provisional application No. 62/053,038, filed on Sep. 19, 2014.

(51) Int. Cl.

| | | |
|---|---|---|
| *A61K 8/42* | (2006.01) | |
| *A61Q 17/02* | (2006.01) | |
| *A61Q 17/04* | (2006.01) | |
| *A61K 8/90* | (2006.01) | |
| *A61K 8/81* | (2006.01) | |

(52) U.S. Cl.
CPC ............. *A61K 8/42* (2013.01); *A61K 8/8152* (2013.01); *A61K 8/90* (2013.01); *A61Q 17/02* (2013.01); *A61Q 17/04* (2013.01); *A61K 2800/5922* (2013.01)

(58) Field of Classification Search
CPC ... A61K 2800/592; A61Q 17/02; A61Q 17/04
See application file for complete search history.

(56) References Cited

U.S. PATENT DOCUMENTS 5,716,602 A * 2/1998 Uick ................... A61K 8/35
424/400
2006/0110419 A1* 5/2006 Keilman ............... A01N 37/18
424/405

OTHER PUBLICATIONS

Soltex Opt. Datasheet [online]. Rohm and Haas, Aug. 2007 [retrieved on Mar. 29, 2016]. Retrieved from the Internet: <http://www.dow.com/assets/attachments/business/pcare/soltex/soltex_opt/tds/soltex_opt.pdf>.*
Dondi et al., "Interactions between different solar UVB/UVA filters contained in commercial suncreams and consequent loss of UV protection", 2006, Photochemical and Photobiological Sciences, vol. 5, pp. 835-843.*
http://wisderm.com/ingredients/Avobenzone entitled "Avobenzone—Avobenzone is one of the best fiiters of UVA radiation, making it a good candidate for sun protection to prevent photoaging", Sep. 24, 2014.

* cited by examiner

*Primary Examiner* — Michael B Pallay
(74) *Attorney, Agent, or Firm* — Withers & Keys, LLC

(57) ABSTRACT

The present invention is directed to combination sunscreen and insect repellant compositions. The combination sunscreen and insect repellant compositions contain (i) diethyl toluamide (or N,N-Diethyl-3-methylbenzamide or DEET), (ii) one or more sunscreen components, with each sunscreen component being capable of absorbing ultraviolet light rays, and (iii) a polymeric binder system of one or more $C_{10\text{-}30}$ alkyl acrylate polymers or co-polymers, and one or more $C_{12\text{-}22}$ alkyl methacrylate polymers or co-polymers. The combination sunscreen and insect repellant compositions may contain additional composition components such as butyloctyl salicylate, a crosslinked polyacrylate polymer, and deionized water. The present invention is also directed to methods of making and using combination sunscreen and insect repellant compositions.

20 Claims, No Drawings

SUNSCREEN/INSECT REPELLANT COMPOSITIONS AND METHODS OF MAKING AND USING THE SAME

CROSS-REFERENCE TO RELATED APPLICATIONS

This patent application claims the benefit of priority to (i) U.S. provisional patent application Ser. No. 62/031,992 entitled "SUNSCREEN/INSECT REPELLANT COMPOSITIONS AND METHODS OF MAKING AND USING THE SAME" filed on Aug. 1, 2014, and (ii) U.S. provisional patent application Ser. No. 62/053,038 entitled "SUNSCREEN/INSECT REPELLANT COMPOSITIONS AND METHODS OF MAKING AND USING THE SAME" filed on Sep. 19, 2014, the subject matter of which is incorporated herein in its entirety.

FIELD OF THE INVENTION

The present invention is directed to sunscreen and insect repellant compositions. The present invention is further directed to methods of making and using sunscreen and insect repellant compositions.

BACKGROUND OF THE INVENTION

Efforts continue to develop sunscreen and insect repellant compositions that provide a broad spectrum of skin protection, as well as insect repellency.

SUMMARY OF THE INVENTION

The present invention relates to the discovery of sunscreen and insect repellant compositions that provide a broad spectrum of skin protection, as well as insect repellency. The sunscreen and insect repellant compositions of the present invention also provide users with a storage-stable composition substantially free of any clumps or agglomerates of material (i.e., a lotion having a desire degree of consistency and free from clumps).

In one exemplary embodiment, the compositions of the present invention comprise a combination sunscreen and insect repellant composition comprising: at least 15 weight percent (wt %) of diethyl toluamide (or N,N-diethyl-3-methylbenzamide or DEET); at least 15 wt % of one or more sunscreen components, each of said one or more sunscreen components being capable of absorbing ultraviolet light rays; and a polymeric binder system comprising: from greater than 0 wt % to about 1.0 wt % of one or more $C_{10\text{-}30}$ alkyl acrylate polymers or co-polymers; and from greater than 0 wt % to about 5.0 wt % of one or more $C_{12\text{-}22}$ alkyl methacrylate polymers or co-polymers; wherein all weight percents are based on a total weight of said composition.

In another exemplary embodiment, the compositions of the present invention comprise a combination sunscreen and insect repellant composition comprising: at least 5 wt % of one or more dihydronepetalactones, one or more dihydronepetalactone derivatives, or any combination thereof; at least 5 wt % of one or more sunscreen components, each of said one or more sunscreen components being capable of absorbing ultraviolet light rays; and a polymeric binder system; wherein all weight percents are based on a total weight of said composition. In some embodiments, the polymeric binder system comprises: from greater than 0 wt % to about 5.0 wt % of one or more $C_{10\text{-}30}$ alkyl acrylate polymers or co-polymers; and from greater than 0 wt % to about 15.0 wt % of one or more $C_{12\text{-}22}$ alkyl methacrylate polymers or co-polymers based on a total weight of said composition.

The present invention is further directed to methods of making sunscreen and insect repellant compositions. In one exemplary embodiment, the method of making a composition comprises mixing the following composition components to form a given composition: at least 15 weight percent (wt %) of diethyl toluamide (or N,N-Diethyl-3-methylbenzamide or DEET); at least 15 wt % of one or more sunscreen components, each of said one or more sunscreen components being capable of absorbing ultraviolet light rays; and a polymeric binder system comprising: from greater than 0 wt % to about 1.0 wt % of one or more $C_{10\text{-}30}$ alkyl acrylate polymers or co-polymers; and from greater than 0 wt % to about 5.0 wt % of one or more $C_{12\text{-}22}$ alkyl methacrylate polymers or co-polymers; wherein all weight percents are based on a total weight of said composition.

In another exemplary embodiment, the method of making a composition comprises mixing the following composition components to form a given composition: at least 5 wt % of one or more dihydronepetalactones, dihydronepetalactone derivatives or any combination thereof; at least 5 wt % of one or more sunscreen components, each of said one or more sunscreen components being capable of absorbing ultraviolet light rays; and a polymeric binder system; wherein all weight percents are based on a total weight of said composition. In some embodiments, the polymeric binder system comprises: from greater than 0 wt % to about 5.0 wt % of one or more $C_{10\text{-}30}$ alkyl acrylate polymers or co-polymers; and from greater than 0 wt % to about 15.0 wt % of one or more $C_{12\text{-}22}$ alkyl methacrylate polymers or co-polymers based on a total weight of said composition.

The present invention is even further directed to methods of using compositions to protect a surface from damaging sunlight. In one exemplary embodiment, the method of using a composition comprises applying a composition onto a skin surface, wherein the composition comprises: at least 15 weight percent (wt %) of diethyl toluamide (or N,N-Diethyl-3-methylbenzamide or DEET); at least 15 wt % of one or more sunscreen components, each of said one or more sunscreen components being capable of absorbing ultraviolet light rays; and a polymeric binder system comprising: from greater than 0 wt % to about 1.0 wt % of one or more $C_{10\text{-}30}$ alkyl acrylate polymers or co-polymers; and from greater than 0 wt % to about 5.0 wt % of one or more $C_{12\text{-}22}$ alkyl methacrylate polymers or co-polymers; wherein all weight percents are based on a total weight of said composition.

In another exemplary embodiment, the method of using a composition comprises applying a composition onto a skin surface, wherein the composition comprises: at least 5 wt % of one or more dihydronepetalactones, dihydronepetalactone derivatives or any combination thereof; at least 5 wt % of one or more sunscreen components, each of said one or more sunscreen components being capable of absorbing ultraviolet light rays; and a polymeric binder system; wherein all weight percents are based on a total weight of said composition. In some embodiments, the polymeric binder system comprises: from greater than 0 wt % to about 5.0 wt % of one or more $C_{10\text{-}30}$ alkyl acrylate polymers or co-polymers; and from greater than 0 wt % to about 15.0 wt % of one or more $C_{12\text{-}22}$ alkyl methacrylate polymers or co-polymers based on a total weight of said composition.

These and other features and advantages of the present invention will become apparent after a review of the following detailed description of the disclosed embodiments and the appended claims.

DETAILED DESCRIPTION OF THE INVENTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

The present invention is directed to sunscreen and insect repellant compositions. The present invention is further directed to methods of making sunscreen and insect repellant compositions. The present invention is even further directed to methods of using sunscreen and insect repellant compositions.

The sunscreen and insect repellant compositions of the present invention provide one or more benefits and/or technical advantages that were not previously addressed in the art of sunscreen and insect repellant compositions. For example, the disclosed sunscreen and insect repellant compositions comprise a combination of UV ray absorbers and a solvent system that enables the formulation of a storage-stable composition containing (1)(i) up to about 40 weight percent (wt %) of diethyltoluamide (DEET) and/or (ii) up to 50 wt % one or more dihydronepetalactones, dihydronepetalactone derivatives or any combination thereof, and (2) up to about 25 wt % of the combination of UV ray absorbers while maintaining a desire degree of product consistency (i.e., is substantially free from clumps/agglomerates).

A description of exemplary sunscreen and insect repellant compositions and composition components is provided below.

I. Sunscreen and Insect Repellant Compositions

The sunscreen and insect repellant compositions of the present invention may comprise a number of individual components. A description of individual components and combinations of individual components is provided below. Further, the sunscreen and insect repellant compositions of the present invention may be presented in various forms. A description of types of compositions is also provided below.

A. Composition Components

The sunscreen and insect repellant compositions of the present invention may comprise (or consist essentially of, or consist of) one or more of the following composition components.

1. UV Ray Absorbers

The sunscreen and insect repellant compositions of the present invention comprise one or more UV ray absorbers. Typically, the sunscreen and insect repellant compositions of the present invention comprise two or more UV ray absorbers, and may comprise as many as five to eight distinct UV ray absorbers. Suitable UV ray absorbers include, but are not limited to, 1-(4-methoxyphenyl)-3-(4-tert-butylphenyl)propane-1,3-dione (i.e., avobenzone); 2-ethylhexyl 2-cyano-3,3-diphenyl-2-propenoate (also referred to as octocrylene); 3,3,5-trimethylcyclohexyl 2-hydroxybenzoate (also referred to as homosalate); (RS)-2-ethylhexyl (2E)-3-(4-methoxyphenyl)prop-2-enoate (also referred to herein as octinoxate); and 2-ethylhexyl 2-hydroxybenzoate (also referred to as octisalate).

The one or more UV ray absorbers are typically present in the compositions of the present invention in a total amount greater than about 10 wt % and up to about 25 wt % based on a total weight of a given composition (or any value between and including 10 and 25 wt %, in increments of 0.01 wt %, e.g., 24.06 wt %, or any range of values between and including 10 and 25 wt %, in increments of 0.01 wt %, e.g., 20.50 to 24.03 wt %). In some exemplary embodiments, a given composition comprises one or more UV ray absorbers in a total amount ranging from about 10 wt % to about 25 wt % based on a total weight of a given composition. In some exemplary embodiments, a given composition comprises one or more UV ray absorbers in a total amount ranging from about 18 wt % to about 24 wt % based on a total weight of a given composition. In other exemplary embodiments, a given composition comprises one or more UV ray absorbers in a total amount ranging from about 22 wt % to about 23.5 wt % based on a total weight of a given composition.

When present, each individual UV ray absorber may be present in equal or varying amounts in the compositions of the present invention. Typically, when present, each individual UV ray absorber is present in an individual amount ranging from greater than 0.0 wt % to about 9.0 wt % based on a total weight of a given composition (or any value between and including 0.01 and 9.0 wt %, in increments of 0.01 wt %, e.g., 4.60 wt %, or any range of values between and including 0.01 and 9.00 wt %, in increments of 0.01 wt %, e.g., 0.05 to 6.18 wt %). More, typically, when present, each individual UV ray absorber is present in an individual amount ranging from about 2.5 wt % to about 7.5 wt % based on a total weight of a given composition.

2. Insect Repellants

The sunscreen and insect repellant compositions of the present invention comprise one or more insect repellants. Suitable insect repellants include, but are not limited to, all insect repellants approved for use by the Environmental Protection Agency (EPA). Such EPA-approved insect repellants include, but are not limited to, diethyl toluamide (or N,N-diethyl-3-methylbenzamide or DEET), dihydronepetalactones, and dihydronepetalactone derivatives. Suitable dihydronepetalactones include, but are not limited to, each of the stereoisomers of dihydronepetalactone disclosed in U.S. Pat. Nos. 7,232,844 and 7,067,677, the subject matter of each of which is hereby incorporated herein in its entirety. Suitable dihydronepetalactone derivatives include, but are not limited to, each of the derivatives of dihydronepetalactone (i.e., dihydronepetalactone substituted with one or more substituents) disclosed in U.S. Pat. No. 7,067,678, the subject matter of which is hereby incorporated herein in its entirety.

When present, the one or more insect repellants are typically present in the compositions of the present invention in a total amount of from about 5 wt % to about 50 wt % based on a total weight of a given composition (or any value between and including 5 and 50 wt %, in increments of 0.01 wt %, e.g., 24.06 wt %, or any range of values between and including 5 and 50 wt %, in increments of 0.01 wt %, e.g., 20.05 to 34.63 wt %). In some exemplary embodiments, a given composition comprises one or more insect repellants (e.g., DEET, one or more dihydronepetalactones, one or more dihydronepetalactone derivatives, or any combination thereof) in a total amount ranging from about 15.0 wt % to about 40.0 wt % based on a total weight of a given composition. In some exemplary embodiments, a given composition comprises one or more insect repellants (e.g., DEET, one or more dihydronepetalactones, one or more dihydronepetalactone derivatives, or any combination thereof) in a total amount ranging from about 20 wt % to about 40.0 wt % based on a total weight of a given composition.

3. Polymeric Binder System

The sunscreen and insect repellant compositions of the present invention further comprise a polymeric binder system. In some embodiments, the polymeric binder system comprises (i) one or more $C_{10-30}$ alkyl acrylate polymers or co-polymers; and (ii) one or more $C_{12-22}$ alkyl methacrylate polymers or co-polymers. Suitable $C_{10-30}$ alkyl acrylate polymers or co-polymers include, but are not limited to, $C_{10-30}$ alkyl acrylate polymers or co-polymers commercially available from Lubrizol (Wickliffe, Ohio) under the trade designation PERMULEN TR-2. Suitable $C_{12-22}$ alkyl methacrylate polymers or co-polymers include, but are not limited to, $C_{12-22}$ alkyl methacrylate polymers or co-polymers commercially available from Dow Chemical (Midland, Mich.) under the trade designation SOLTEX OPT.

Each of the (i) one or more $C_{10-30}$ alkyl acrylate polymers or co-polymers and (ii) one or more $C_{12-22}$ alkyl methacrylate polymers or co-polymers are typically present in the compositions of the present invention in an amount greater than 0 wt % and up to about 25.0 wt % based on a total weight of a given composition (or any value between and including 0.01 and 25.0 wt %, in increments of 0.01 wt %, e.g., 24.06 wt %, or any range of values between and including 0.01 and 25 wt %, in increments of 0.01 wt %, e.g., 20.05 to 24.53 wt %). In some exemplary embodiments, each of the (i) one or more $C_{10-30}$ alkyl acrylate polymers or co-polymers and (ii) one or more $C_{12-22}$ alkyl methacrylate polymers or co-polymers are independently present in the compositions of the present invention in an amount of from about 0.10 wt % to about 3.5 wt % based on a total weight of a given composition. In some exemplary embodiments, each of the (i) one or more $C_{10-30}$ alkyl acrylate polymers or co-polymers and (ii) one or more $C_{12-22}$ alkyl methacrylate polymers or co-polymers are independently present in the compositions of the present invention in an amount of from about 0.25 wt % to about 2.5 wt % based on a total weight of a given composition. In other exemplary embodiments, the one or more $C_{10-30}$ alkyl acrylate polymers or co-polymers are present in an amount of from about 0.25 wt % and the one or more $C_{12-22}$ alkyl methacrylate polymers or co-polymers are present in an amount of about 2.1 wt % based on a total weight of a given composition.

4. Water

The sunscreen and insect repellant compositions of the present invention may further comprise water (e.g., deionized water). When present, water is typically present in the compositions of the present invention in a total amount greater than 0 wt % and up to about 50 wt % based on a total weight of a given composition (or any value between and including 0.01 and 50 wt %, in increments of 0.01 wt %, e.g., 24.06 wt %, or any range of values between and including 0.01 and 50 wt %, in increments of 0.01 wt %, e.g., 20.05 to 24.53 wt %). In some exemplary embodiments, a given composition comprises water in a total amount ranging from about 35 to about 45 wt % based on a total weight of a given composition. In some exemplary embodiments, a given composition comprises water in a total amount ranging from about 40 wt % to about 44 wt % based on a total weight of a given composition. In other exemplary embodiments, a given composition comprises water in a total amount of about 42.0 to about 43.0 wt % based on a total weight of a given composition.

5. Co-Solvent System Components

The sunscreen and insect repellant compositions of the present invention may further comprise one or more co-solvents. Suitable co-solvents include, but are not limited to, butyloctyl salicylate, propanediol, and combinations thereof. Suitable commercially available butyloctyl salicylates include, but are not limited to, butyloctyl salicylate commercially available from Hallstar (Chicago, Ill.) under the trade designation HALLBRITE BHB. Suitable commercially available propanediols include, but are not limited to, propanediol commercially available from Dow Chemical (Midland, Mich.) under the trade designation ZEMEA.

Each of the one or more co-solvents is typically present in the compositions of the present invention in an amount greater than 0 wt % and up to about 10.0 wt % based on a total weight of a given composition (or any value between and including 0.01 and 10.0 wt %, in increments of 0.01 wt %, e.g., 4.06 wt %, or any range of values between and including 0.01 and 10.0 wt %, in increments of 0.01 wt %, e.g., 6.05 to 7.53 wt %). In some exemplary embodiments, each of the one or more co-solvents is independently present in the compositions of the present invention in an amount of from about 2.0 wt % to about 7.5 wt % based on a total weight of a given composition. In some exemplary embodiments, each of the one or more co-solvents is independently present in the compositions of the present invention in an amount of from about 2.0 wt % to about 5.0 wt % based on a total weight of a given composition. In other exemplary embodiments, the one or more co-solvents comprises butyloctyl salicylate commercially available from Hallstar (Chicago, Ill.) under the trade designation HALLBRITE BHB in an amount of about 5.0 wt % based on a total weight of a given composition in combination with propanediol commercially available from Dow Chemical (Midland, Mich.) under the trade designation ZEMEA in an amount of about 2.0 wt % based on a total weight of a given composition.

6. Additives

The sunscreen and insect repellant compositions of the present invention may further comprise one or more additives. Suitable additives include, but are not limited to, thickeners, chelating agents, skin treatments, emulsifiers, pH adjusters, antimicrobials, fragrances, and any combination thereof.

When present, each of the one or more additives is typically present in the compositions of the present invention in an amount greater than 0 wt % and up to about 2.0 wt % based on a total weight of a given composition (or any value between and including 0.01 and 2.0 wt %, in increments of 0.01 wt %, e.g., 1.06 wt %, or any range of values between and including 0.01 and 2.0 wt %, in increments of 0.01 wt %, e.g., 0.05 to 4.53 wt %). In some exemplary embodiments, each of the one or more additives is independently present in the compositions of the present invention in an amount of from about 0.01 wt % to about 1.00 wt % based on a total weight of a given composition.

In some exemplary embodiments, a thickener (e.g., a crosslinked polyacrylate polymer commercially available from DuPont (Wilmington, Del.) under the trade designation CARBOPOL 980) is present in an amount ranging from about 0.05 wt % to about 1.0 wt %, more typically, from about 0.10 wt % to about 0.25 wt %, based on a total weight of a given composition.

In some exemplary embodiments, an antimicrobial (e.g., a mixture of phenoxyethanol, chlorphenesin and caprylyl glycol commercially available from DuPont (Wilmington, Del.) under the trade designation MIKROKILL COS) is present in an amount ranging from about 0.25 wt % to about 3.0 wt %, more typically, from about 0.90 wt % to about 1.10 wt %, based on a total weight of a given composition.

In some exemplary embodiments, a pH adjuster (e.g., a sodium hydroxide, 25 wt % solution) is present in an amount ranging from greater than 0 wt % to about 1.0 wt %, more typically, from about 0.50 wt % to about 0.75 wt %, based on a total weight of a given composition.

In some exemplary embodiments, an emulsifier (e.g., a mixture of potassium cetyl phosphate and hydrogenated palm glycerides commercially available from Vigon International, Inc. (East Stroudsburg, Pa.) under the trade designation EMUSIPHOS) is present in an amount ranging from greater than 0 wt % to about 5.0 wt %, more typically, from about 2.5 wt % to about 3.5 wt %, based on a total weight of a given composition.

In some exemplary embodiments, a chelating agent (e.g., disodium ethylenediaminetetraacetic acid (EDTA)) is present in an amount ranging from greater than 0 wt % to about 1.0 wt %, more typically, from about 0.05 wt % to about 0.2 wt %, based on a total weight of a given composition.

In some exemplary embodiments, a skin treatment (e.g., tocopheryl acetate commercially available from Jeen International Corp. (Fairfield, N.J.) is present in an amount ranging from greater than 0 wt % to about 2.0 wt %, more typically, from about 0.05 wt % to about 0.2 wt %, based on a total weight of a given composition.

In some exemplary embodiments, a fragrance (e.g., citronella extract commercially available from Citrus & Allied Essences LTD. (Lake Success, N.Y.) is present in an amount ranging from greater than 0 wt % to about 1.0 wt %, more typically, from about 0.01 wt % to about 0.25 wt %, based on a total weight of a given composition.

B. Composition Forms

The compositions of the present invention may be present as a liquid composition (e.g., an oil-in-water emulsion), or a paste or lotion composition, or as oils, pomades, ointments, gels and sprays.

II. Methods of Making Compositions

The present invention is further directed to methods of making compositions. In one exemplary embodiment, the method of making a composition comprises mixing any of the disclosed composition components to form a given composition. Typically, the mixing step comprises high shear mixing of two or more of the herein described composition components.

In one exemplary embodiment, the method of making a composition comprises: dispersing a crosslinked polyacrylate polymer (e.g., CARBOPOL® 980) and one or more $C_{10-30}$ alkyl acrylate polymers or co-polymers (e.g., PEMULEN® TR-2) in water to form a first mixture; adding propanediol and EDTA to the first mixture; heating the first mixture to about 70-75° C. and mixing until uniform; mixing an insect repellant (e.g., DEET, one or more dihydronepetalactones, one or more dihydronepetalactone derivatives, or any combination thereof), one or more sunscreens including avobenzone, butyl octyl salicylate and vitamin E to form a second mixture; heating the second mixture to about 70-75° C. and mixing until the avobenzone dissolves; adding a mixture of potassium cetyl phosphate and hydrogenated palm glycerides (e.g., EMUSIPHOS) to the second mixture and mixing at about 70-75° C. until uniform; adding the second mixture (e.g., oil phase) to the first mixture (e.g., the water phase) and mixing at about 70-75° C. until uniform; cooling the composition to about 60-65° C.; adding sodium hydroxide; cooling while mixing to about 40-45° C.; adding any remaining ingredients (e.g., 1-(4-methoxyphenyl)-3-(4-tert-butylphenyl)propane-1,3-dione (e.g., PARSOL 1789), a mixture of phenoxyethanol, chlorphenesin and caprylyl glycol (e.g., MIKROKILL COS), citronella extract, and one or more $C_{12-22}$ alkyl methacrylate polymers or co-polymers (e.g., SOLTEX OPT)) one at a time; and mixing while cooling to about 25° C.

III. Applications/Uses

The present invention is further directed to methods of using the disclosed compositions to provide sun protection and insect protection. In one exemplary embodiment, the method of using a composition comprises applying any of the herein-described combination sunscreen and insect repellant compositions onto a skin surface.

The methods of using combination sunscreen and insect repellant compositions of the present invention may further comprise one or more additional method steps. Suitable additional method steps include, but are not limited to, cleaning a surface (e.g., skin) prior to applying a given combination sunscreen and insect repellant composition of the present invention onto the surface; and washing the sunscreen/insect repellant composition off of the surface.

Exemplary combination sunscreen and insect repellant compositions of the present invention are provided below.

Additional Embodiments

Combination Sunscreen and Insect Repellant Compositions

1. A combination sunscreen and insect repellant composition comprising: at least 15 weight percent (wt %) of diethyl toluamide (or N,N-Diethyl-3-methylbenzamide or DEET); at least 15 wt % of one or more sunscreen components, each of said one or more sunscreen components being capable of absorbing ultraviolet light rays; and a polymeric binder system comprising: from greater than 0 wt % to about 1.0 wt % of one or more $C_{10-30}$ alkyl acrylate polymers or co-polymers; and from greater than 0 wt % to about 5.0 wt % of one or more $C_{12-22}$ alkyl methacrylate polymers or co-polymers; wherein all weight percents are based on a total weight of said composition. DEET is typically present in a total amount of from about 15 wt % to about 50 wt % based on a total weight of a given composition (or any value between and including 15 and 50 wt %, in increments of 0.01 wt %, e.g., 24.06 wt %, or any range of values between and including 15 and 50 wt %, in increments of 0.01 wt %, e.g., 20.05 to 34.63 wt %). The sunscreen components are typically present in a total amount of from about 15 wt % to about 25 wt % based on a total weight of a given composition (or any value between and including 15 and 25 wt %, in increments of 0.01 wt %, e.g., 24.06 wt %, or any range of values between and including 15 and 25 wt %, in increments of 0.01 wt %, e.g., 20.05 to 24.63 wt %).

2. A combination sunscreen and insect repellant composition comprising: at least 5 wt % of one or more dihydronepetalactones, one or more dihydronepetalactone derivatives, or any combination thereof; at least 5 wt % of one or more sunscreen components, each of said one or more sunscreen components being capable of absorbing ultraviolet light rays; and a polymeric binder system; wherein all weight percents are based on a total weight of said composition. In some embodiments, the "one or more dihydronepetalactones, one or more dihydronepetalactone derivatives, or any combination thereof" may comprise any one or any combination of the dihydronepetalactones and dihydronepetalactone derivatives disclosed in U.S. Pat. Nos. 7,067,677; 7,067,678; and 7,232,844.

3. The composition of embodiment 2, wherein said polymeric binder system comprising: from greater than 0 wt % to about 5.0 wt % of one or more $C_{10-30}$ alkyl acrylate polymers or co-polymers; and from greater than 0 wt % to about 10.0 wt % of one or more $C_{12-22}$ alkyl methacrylate polymers or co-polymers; wherein all weight percents are based on a total weight of said composition.

4. The composition of embodiment 1, wherein said diethyl toluamide is present in an amount of at least 18 wt %, and said one or more sunscreen components are present in an amount of at least 18 wt %.

5. The composition of embodiment 1 or 4, wherein said diethyl toluamide is present in an amount of about 20 wt %, and said one or more sunscreen components are present in an amount of about 23.25 wt %.

6. The composition of embodiment 2 or 3, wherein said one or more dihydronepetalactones, one or more dihydronepetalactone derivatives, or any combination thereof being present in an amount of at least 10 wt %, and said one or more sunscreen components are present in an amount of at least 10 wt %.

7. The composition of any one of embodiments 2, 3 or 6, wherein said one or more dihydronepetalactones, one or more dihydronepetalactone derivatives, or any combination thereof being present in an amount of about 20 wt %, and said one or more sunscreen components are present in an amount of about 23.25 wt %.

8. The composition of any one of embodiments 1 to 7, wherein said one or more sunscreen components comprises at least one broad spectrum sunscreen component that absorbs UV-A and UV-B light rays.

9. The composition of embodiment 8, wherein said at least one broad spectrum sunscreen component comprises 1-(4-methoxyphenyl)-3-(4-tert-butylphenyl)propane-1,3-dione (i.e., avobenzone).

10. The composition of any one of embodiments 1 to 9, wherein said one or more sunscreen components comprise (i) 2-ethylhexyl 2-cyano-3,3-diphenyl-2-propenoate (also referred to as octocrylene), (ii) 3,3,5-trimethylcyclohexyl 2-hydroxybenzoate (also referred to as homosalate), (iii) (RS)-2-ethylhexyl (2E)-3-(4-methoxyphenyl)prop-2-enoate (also referred to herein as octinoxate), (iv) 2-ethylhexyl 2-hydroxybenzoate (also referred to as octisalate), or (v) any combination of (i) to (iv).

11. The composition of any one of embodiments 1 to 10, wherein said one or more sunscreen components comprise (i) 2-ethylhexyl 2-cyano-3,3-diphenyl-2-propenoate, (ii) 3,3,5-trimethylcyclohexyl 2-hydroxybenzoate, (iii) (RS)-2-ethylhexyl (2E)-3-(4-methoxyphenyl)prop-2-enoate, and (iv) 2-ethylhexyl 2-hydroxybenzoate.

12. The composition of any one of embodiments 1 to 11, wherein each sunscreen component is present in an amount of greater than about 2.5 wt %.

13. The composition of any one of embodiments 1 to 12, wherein each sunscreen component is present in an amount of greater than about 2.75 wt %.

14. The composition of any one of embodiments 10 to 13, wherein each of said 3,3,5-trimethylcyclohexyl 2-hydroxybenzoate, said (RS)-2-ethylhexyl (2E)-3-(4-methoxyphenyl)prop-2-enoate, and said 2-ethylhexyl 2-hydroxybenzoate, when present, independently comprises from about 3.0 wt % to about 9.0 wt % of said composition.

15. The composition of any one of embodiments 10 to 14, wherein each of said 3,3,5-trimethylcyclohexyl 2-hydroxybenzoate, said (RS)-2-ethylhexyl (2E)-3-(4-methoxyphenyl)prop-2-enoate, and said 2-ethylhexyl 2-hydroxybenzoate, when present, independently comprises from about 5.0 wt % to about 7.5 wt % of said composition.

16. The composition of any one of embodiments 1 to 15, wherein said one or more sunscreen components comprises: about 3.0 wt % of 1-(4-methoxyphenyl)-3-(4-tert-butylphenyl)propane-1,3-dione (i.e., avobenzone); about 2.75 wt % of 2-ethylhexyl 2-cyano-3,3-diphenyl-2-propenoate; about 5.0 wt % of 3,3,5-trimethylcyclohexyl 2-hydroxybenzoate, about 7.5 wt % of (RS)-2-ethylhexyl (2E)-3-(4-methoxyphenyl)prop-2-enoate; and about 5.0 wt % of 2-ethylhexyl 2-hydroxybenzoate.

17. The composition of any one of embodiments 1 to 16, further comprising: a crosslinked polyacrylate polymer (i.e., CARBOPOL 980) in an amount ranging from greater than 0 wt % to about 2.0 wt % of said composition.

18. The composition of any one of embodiments 1 to 17, further comprising: a sodium hydroxide solution in an amount ranging from greater than 0 wt % to about 1.0 wt % of said composition.

19. The composition of any one of embodiments 1 and 3 to 18, wherein said one or more $C_{12-22}$ alkyl methacrylate polymers or co-polymers comprises a co-polymer resulting from polymerization of: methacrylic acid, methyl methacrylate, butyl acrylate, and cetyl-eicosinyl methacrylate monomers (i.e., SOLTEX OPT).

20. The composition of any one of embodiments 1 and 3 to 19, wherein said one or more $C_{10-30}$ alkyl acrylate polymers or co-polymers or a crosslinked combination of polymers and/or co-polymers or block co-polymers. In some desired embodiments, the $C_{10-30}$ alkyl co-polymer comprises a copolymer having the chemical structure below

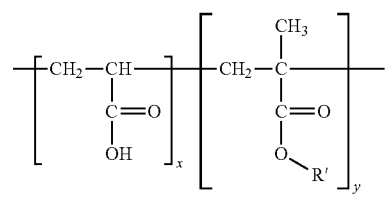

where x and y each independently comprise a number ranging from greater than 0 to 100.0 (or any number between greater than 0 and 10.0 including 0.01 and 100.0, in increments of 0.01, e.g., 12.15, or any range of numbers between greater than 0 and 100.0 including 0.01 and 100.0, in increments of 0.01, e.g., from about 1.00 to about 3.25), and R' represents an alkyl group having from about 10 to about 30 carbon atoms. In some embodiments, y is greater than x. In some embodiments, the $C_{10\text{-}30}$ alkyl co-polymer is PEMULEN TR-2 copolymer commercially available from Lubrizol (Wickliffe, Ohio).

21. The composition of any one of embodiments 1 to 20, further comprising: butyloctyl salicylate in an amount ranging from greater than 0 wt % to about 8.0 wt % of said composition.

22. The composition of any one of embodiments 1 to 21, further comprising: a mixture of potassium cetyl phosphate and hydrogenated palm glycerides (i.e., EMUSIPHOS) in an amount ranging from greater than 0 wt % to about 5.0 wt % of said composition.

23. The composition of any one of embodiments 1 to 21, further comprising: a mixture of phenoxyethanol, chlorphenesin and caprylyl glycol (i.e., MIKROKILL COS) in an amount ranging from greater than 0 wt % to about 3.0 wt % of said composition.

24. The composition of any one of embodiments 1 to 23, further comprising: propanediol in an amount ranging from greater than 0 wt % to about 5.0 wt % of said composition.

25. The composition of any one of embodiments 1 to 24, further comprising: disodium ethylenediaminetetraacetic acid (EDTA) in an amount ranging from greater than 0 wt % to about 1.0 wt % of said composition.

26. The composition of any one of embodiments 1 to 25, further comprising: tocopheryl acetate in an amount ranging from greater than 0 wt % to about 2.0 wt % of said composition.

27. The composition of any one of embodiments 1 to 26, further comprising: citronella extract in an amount ranging from greater than 0 wt % to about 1.0 wt % of said composition.

28. The composition of any one of embodiments 1 to 27, further comprising: deionized water in an amount ranging from greater than 0 wt % to about 60.0 wt % of said composition.

29. The composition of any one of embodiments 1 to 28, further comprising: deionized water in an amount ranging from about 40.0 wt % to about 50.0 wt % of said composition.

30. The composition of any one of embodiments 1, 4 to 5, and 8 to 29, wherein said composition comprises components and amounts as shown below:

| Component | Amount |
| --- | --- |
| deionized water | 42.4 wt % |
| a crosslinked polyacrylate polymer (i.e., CARBOPOL 980) | 0.15 wt % |
| propanediol | 2.0 wt % |
| disodium EDTA | 0.10 wt % |
| one or more $C_{10\text{-}30}$ alkyl acrylate polymers or co-polymers | 0.25 wt % |
| DEET | 20.0 wt % |
| 2-ethylhexyl 2-cyano-3,3-diphenyl-2-propenoate | 2.75 wt % |
| 3,3,5-trimethylcyclohexyl 2-hydroxybenzoate | 5.0 wt % |
| butyloctyl salicylate | 5.0 wt % |
| (RS)-2-ethylhexyl (2E)-3-(4-methoxyphenyl)prop-2-enoate | 7.5 wt % |
| 2-ethylhexyl 2-hydroxybenzoate | 5.0 wt % |
| tocopheryl acetate | 0.10 wt % |
| 1-(4-methoxyphenyl)-3-(4-tert-butylphenyl)propane-1,3-dione | 3.0 wt % |
| a mixture of potassium cetyl phosphate and hydrogenated palm glycerides | 3.0 wt % |
| sodium hydroxide solution (20 wt % NaOH in water) | 0.65 wt % |
| a mixture of phenoxyethanol, chlorphenesin and caprylyl glycol | 1.0 wt % |
| citronella extract | 0.01 wt % |
| one or more $C_{12\text{-}22}$ alkyl methacrylate polymers or co-polymers | 2.10 wt % | wherein all weight percents are based on a total weight of said composition.

31. The composition of any one of embodiments 2 to 3 and 6 to 29, wherein said composition comprises components and amounts as shown below:

| Component | Amount |
| --- | --- |
| deionized water | 42.4 wt % |
| a crosslinked polyacrylate polymer (i.e., CARBOPOL 980) | 0.15 wt % |
| propanediol | 2.0 wt % |
| disodium EDTA | 0.10 wt % |
| one or more $C_{10\text{-}30}$ alkyl acrylate polymers or co-polymers | 0.25 wt % |
| one or more dihydronepetalactones, one or more dihydronepetalactone derivatives, or any combination thereof | 20.0 wt % |
| 2-ethylhexyl 2-cyano-3,3-diphenyl-2-propenoate | 2.75 wt % |
| 3,3,5-trimethylcyclohexyl 2-hydroxybenzoate | 5.0 wt % |
| butyloctyl salicylate | 5.0 wt % |
| (RS)-2-ethylhexyl (2E)-3-(4-methoxyphenyl)prop-2-enoate | 7.5 wt % |
| 2-ethylhexyl 2-hydroxybenzoate | 5.0 wt % |
| tocopheryl acetate | 0.10 wt % |
| 1-(4-methoxyphenyl)-3-(4-tert-butylphenyl)propane-1,3-dione | 3.0 wt % |
| a mixture of potassium cetyl phosphate and hydrogenated palm glycerides | 3.0 wt % |
| sodium hydroxide solution (20 wt % NaOH in water) | 0.65 wt % |
| a mixture of phenoxyethanol, chlorphenesin and caprylyl glycol | 1.0 wt % |
| citronella extract | 0.01 wt % |
| one or more $C_{12\text{-}22}$ alkyl methacrylate polymers or co-polymers | 2.10 wt % | wherein all weight percents are based on a total weight of said composition.

Methods of Making Combination Sunscreen and Insect Repellant Compositions

32. A method of making the composition of any one of embodiments 1 to 31, said method comprising: blending composition components so as to form an oil-in-water emulsion.

Methods of Using Combination Sunscreen and Insect Repellant Compositions

33. A method of using the composition of any one of embodiments 1 to 31, said method comprising: applying the composition onto skin of a mammal.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Preparation of Compositions

Compositions were prepared using the components as shown in Table 1 below.

TABLE 1

Exemplary Base Compositions

| Component | Tradename | Supplier | Amount |
|---|---|---|---|
| deionized water | | | 42.4 wt % |
| a crosslinked polyacrylate polymer | CARBOPOL ® 980 | Lubrizol (Wickliffe, OH) | 0.15 wt % |
| propanediol | | DuPont (Wilmington, DE) | 2.0 wt % |
| disodium EDTA | | Dow Chemical (Midland, MI) Univar (Redmund, WA) | 0.10 wt % |
| one or more $C_{10-30}$ alkyl acrylate polymers or co-polymers | PEMULEN ® TR-2 | Lubrizol (Wickliffe, OH) | 0.25 wt % |
| DEET | | McLaughlin Gormley King Company (Golden Valley, MN) | 20.0 wt % |
| 2-ethylhexyl 2-cyano-3,3-diphenyl-2-propenoate | NEO HELIOPAN 303 | Vigon International, Inc. (East Stroudsburg, PA) | 2.75 wt % |
| 3,3,5-trimethyl-cyclohexyl 2-hydroxybenzoate | NEO HELIOPAN HMS | Vigon International, Inc. (East Stroudsburg, PA) | 5.0 wt % |
| butyloctyl salicylate | HALLBRITE BHB | Hallstar (Chicago, IL) | 5.0 wt % |
| (RS)-2-ethylhexyl (2E)-3-(4-methoxy-phenyl)prop-2-enoate | NEO HELIOPAN AV | Vigon International, Inc. (East Stroudsburg, PA) | 7.5 wt % |
| 2-ethylhexyl 2-hydroxybenzoate | NEO HELIOPAN OS/BP | Vigon International, Inc. (East Stroudsburg, PA) | 5.0 wt % |
| tocopheryl acetate | | Jeen International Corp. (Fairfield, NJ) | 0.10 wt % |
| 1-(4-methoxy-phenyl)-3-(4-tert-butylphenyl)propane-1,3-dione | PARSOL 1789 | Nexeo Solutions (The Woodlands, TX) | 3.0 wt % |
| a mixture of potassium cetyl phosphate and hydrogenated palm glycerides | EMULSIPHOS | Vigon International, Inc. (East Stroudsburg, PA) | 3.0 wt % |
| sodium hydroxide solution (20 wt % NaOH in water) | | PCI Scientific Supply, Inc. (Fairfield, NJ) | 0.65 wt % |
| a mixture of phenoxyethanol, chlorphenesin and caprylyl glycol | MIKROKILL COS | Lonza Group (Basel, Switzerland) | 1.0 wt % |
| citronella extract | | Citrus & Allied Essences LTD. (Lake Success, NY) | 0.01 wt % |
| one or more $C_{12-22}$ alkyl methacrylate polymers or co-polymers | SOLTEX OPT | Dow Chemical (Midland, MI) | 2.10 wt % |

The composition was formed using the following method steps:
- dispersing CARBOPOL® 980 and PEMULEN® TR-2 in water to form a first mixture;
- adding propanediol and sodium EDTA to the first mixture;
- heating the first mixture to about 70-75° C. and mixing until uniform;
- mixing DEET, one or more sunscreens including (i) NEO HELIOPAN 303, (ii) NEO HELIOPAN HMS, (iii) NEO HELIOPAN AV, (iv) NEO HELIOPAN OS/BP, and (v) PARSOL 1789, butyl octyl salicylate and tocopheryl acetate to form a second mixture;
- heating the second mixture to about 70-75° C. and mixing until the PARSOL 1789 dissolves;
- adding EMUSIPHOS to the second mixture and mixing at about 70-75° C. until uniform;
- adding the second mixture (e.g., oil phase) to the first mixture (e.g., the water phase) and mixing at about 70-75° C. until uniform;
- cooling the composition to about 60-65° C.;
- adding sodium hydroxide; cooling while mixing to about 40-45° C.;
- adding MIKROKILL COS, citronella extract and SOLTEX OPT, one at a time, in any order; and
- mixing while cooling to about 25° C.

The resulting composition comprised a viscous gelled cream with a citronella odor. The pH of the composition ranged from 6.0-6.5 and the viscosity was 100,000-140,000 cps.

Example 2

Preparation of Compositions

Compositions were prepared using the components as shown in Table 2 below, as well as the mixing steps discussed in Example 1 except a dihydronepetalactone is substituted for DEET.

TABLE 2

Exemplary Base Compositions

| Component | Tradename | Supplier | Amount |
|---|---|---|---|
| deionized water | | | 42.4 wt % |
| a crosslinked polyacrylate polymer | CARBOPOL ® 980 | Lubrizol (Wickliffe, OH) | 0.15 wt % |
| propanediol | | DuPont (Wilmington, DE) | 2.0 wt % |
| disodium EDTA | | Dow Chemical (Midland, MI) Univar (Redmund, WA) | 0.10 wt % |
| one or more $C_{10-30}$ alkyl acrylate polymers or co-polymers | PEMULEN ® TR-2 | Lubrizol (Wickliffe, OH) | 0.25 wt % |

TABLE 2-continued

Exemplary Base Compositions

| Component | Tradename | Supplier | Amount |
|---|---|---|---|
| dihydrone-petalactone | | DuPont (Wilmington, DE) | 20.0 wt % |
| 2-ethylhexyl 2-cyano-3,3-diphenyl-2-propenoate | NEO HELIOPAN 303 | Vigon International, Inc. (East Stroudsburg, PA) | 2.75 wt % |
| 3,3,5-trimethyl-cyclohexyl 2-hydroxybenzoate | NEO HELIOPAN HMS | Vigon International, Inc. (East Stroudsburg, PA) | 5.0 wt % |
| butyloctyl salicylate | HALLBRITE BHB | Hallstar (Chicago, IL) | 5.0 wt % |
| (RS)-2-ethylhexyl (2E)-3-(4-methoxy-phenyl)prop-2-enoate | NEO HELIOPAN AV | Vigon International, Inc. (East Stroudsburg, PA) | 7.5 wt % |
| 2-ethylhexyl 2-hydroxybenzoate | NEO HELIOPAN OS/BP | Vigon International, Inc. (East Stroudsburg, PA) | 5.0 wt % |
| tocopheryl acetate | | Jeen International Corp. (Fairfield, NJ) | 0.10 wt % |
| 1-(4-methoxy-phenyl)-3-(4-tert-butylphenyl)propane-1,3-dione | PARSOL 1789 | Nexeo Solutions (The Woodlands, TX) | 3.0 wt % |
| a mixture of potassium cetyl phosphate and hydrogenated palm glycerides | EMULSIPHOS | Vigon International, Inc. (East Stroudsburg, PA) | 3.0 wt % |
| sodium hydroxide solution (20 wt % NaOH in water) | | PCI Scientific Supply, Inc. (Fairfield, NJ) | 0.65 wt % |
| a mixture of phenoxyethanol, chlorphenesin and caprylyl glycol | MIKROKILL COS | Lonza Group (Basel, Switzerland) | 1.0 wt % |
| citronella extract | | Citrus & Allied Essences LTD. (Lake Success, NY) | 0.01 wt % |
| one or more $C_{12-22}$ alkyl methacrylate polymers or co-polymers | SOLTEX OPT | Dow Chemical (Midland, MI) | 2.10 wt % |

It should be understood that although the above-described combination sunscreen and insect repellant compositions and/or methods are described as "comprising" one or more components or steps, the above-described combination sunscreen and insect repellant compositions and/or methods may "comprise," "consists of," or "consist essentially of" the above-described components, features or steps of the combination sunscreen and insect repellant compositions and/or methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, a combination sunscreen and insect repellant composition and/or method that "comprises" a list of elements (e.g., components, features, or steps) is not necessarily limited to only those elements (or components or steps), but may include other elements (or components or steps) not expressly listed or inherent to the combination sunscreen and insect repellant composition and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a combination sunscreen and insect repellant composition and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described combination sunscreen and insect repellant compositions and/or methods may comprise, consist essentially of, or consist of any of the herein-described components, features and steps, with or without any additional feature(s). In other words, in some embodiments, the combination sunscreen and insect repellant compositions and/or methods of the present invention do not have any additional features other than those described herein, and such additional features are specifically excluded from the combination sunscreen and insect repellant compositions and/or methods. In other embodiments, the combination sunscreen and insect repellant compositions and/or methods of the present invention do have one or more additional features other than those described herein.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A combination sunscreen and insect repellant composition comprising:
    at least 15 weight percent (wt %) of diethyl toluamide (or N,N-Diethyl-3-methylbenzamide or DEET);
    at least 15 wt % of one or more sunscreen components, each of said one or more sunscreen components being capable of absorbing ultraviolet light rays, and wherein said one or more sunscreen components comprises (a) at least one broad spectrum sunscreen component that absorbs UV-A and UV-B light rays, said at least one broad spectrum sunscreen component comprising 1-(4-methoxyphenyl)-3-(4-tert-butylphenyl)propane-1,3-dione and (b) (RS)-2-ethylhexyl (2E)-3-(4-methoxyphenyl)prop-2-enoate; and a polymeric binder system comprising:
  from greater than 0 wt % to about 1.0 wt % of one or more $C_{10-30}$ alkyl acrylate polymers or co-polymers; and
  from greater than 0 wt % to about 5.0 wt % of one or more $C_{12-22}$ alkyl methacrylate polymers or co-polymers;
wherein all weight percents are based on a total weight of said composition.

2. The composition of claim 1, wherein said diethyl toluamide is present in an amount of at least 18 wt %, and said one or more sunscreen components are present in an amount of at least 18 wt %.

3. The composition of claim 1, wherein said one or more sunscreen components further comprise (i) 2-ethylhexyl 2-cyano-3,3-diphenyl-2-propenoate, (ii) 3,3,5-trimethylcyclohexyl 2-hydroxybenzoate, and (iii) 2 ethylhexyl 2-hydroxybenzoate.

4. The composition of claim 1, wherein said one or more sunscreen components comprises:
  about 3.0 wt % of 1-(4-methoxyphenyl)-3-(4-tert-butylphenyl)propane-1,3-dione;
  about 2.75 wt % of 2-ethylhexyl 2-cyano-3,3-diphenyl-2-propenoate;
  about 5.0 wt % of 3,3,5-trimethylcyclohexyl 2-hydroxybenzoate,
  about 7.5 wt % of (RS)-2-ethylhexyl (2E)-3-(4-methoxyphenyl)prop-2-enoate; and
  about 5.0 wt % of 2-ethylhexyl 2-hydroxybenzoate.

5. The composition of claim 1, further comprising: a crosslinked polyacrylate polymer in an amount ranging from greater than 0 wt % to about 2.0 wt % of said composition.

6. The composition of claim 5, further comprising butyloctyl salicylate in an amount ranging from greater than 0 wt % to about 8.0 wt % of said composition.

7. The composition of claim 6, further comprising:
  a mixture of potassium cetyl phosphate and hydrogenated palm glycerides in an amount ranging from greater than 0 wt % to about 5.0 wt % of said composition;
  a mixture of phenoxyethanol, chlorphenesin and caprylyl glycol in an amount ranging from greater than 0 wt % to about 3.0 wt % of said composition; and
  deionized water in an amount ranging from greater than 0 wt % to about 60.0 wt % of said composition.

8. The composition of claim 1, wherein said one or more $C_{12-22}$ alkyl methacrylate polymers or co-polymers comprises a co-polymer resulting from polymerization of: methacrylic acid, methyl methacrylate, butyl acrylate, and cetyl-eicosinyl methacrylate monomers.

9. The composition of claim 1, wherein said one or more $C_{10-30}$ alkyl acrylate polymers or co-polymers comprises a block co-polymer.

10. The composition of claim 1, further comprising:
  butyloctyl salicylate in an amount ranging from greater than 0 wt % to about 8.0 wt % of said composition;
  a mixture of potassium cetyl phosphate and hydrogenated palm glycerides in an amount ranging from greater than 0 wt % to about 5.0 wt % of said composition;
  a mixture of phenoxyethanol, chlorphenesin and caprylyl glycol in an amount ranging from greater than 0 wt % to about 3.0 wt % of said composition;
  propanediol in an amount ranging from greater than 0 wt % to about 5.0 wt % of said composition;
  disodium ethylenediaminetetraacetic acid (EDTA) in an amount ranging from greater than 0 wt % to about 1.0 wt % of said composition;
  tocopheryl acetate in an amount ranging from greater than 0 wt % to about 2.0 wt % of said composition;
  citronella extract in an amount ranging from greater than 0 wt % to about 1.0 wt % of said composition; and
  deionized water in an amount ranging from greater than 0 wt % to about 60.0 wt % of said composition.

11. The composition of claim 10, further comprising: deionized water in an amount ranging from about 40.0 wt % to about 50.0 wt % of said composition.

12. The composition of claim 1, further comprising butyloctyl salicylate in an amount ranging from greater than 0 wt % to about 8.0 wt % of said composition.

13. The composition of claim 1, further comprising:
  a mixture of potassium cetyl phosphate and hydrogenated palm glycerides in an amount ranging from greater than 0 wt % to about 5.0 wt % of said composition;
  a mixture of phenoxyethanol, chlorphenesin and caprylyl glycol in an amount ranging from greater than 0 wt % to about 3.0 wt % of said composition; and
  deionized water in an amount ranging from greater than 0 wt % to about 60.0 wt % of said composition.

14. A method of using the composition of claim 1, said method comprising:
  applying the composition onto skin of a mammal.

15. A combination sunscreen and insect repellant composition comprising components and amounts as shown below:

| Component | Amount |
| --- | --- |
| deionized water | greater than 0 wt % to about 60.0 wt % |
| a crosslinked polyacrylate polymer | greater than 0 wt % to about 2.0 wt % |
| propanediol | greater than 0 wt % to about 5.0 wt % |
| disodium EDTA | greater than 0 wt % to about 1.0 wt % |
| one or more $C_{10-30}$ alkyl acrylate polymers or co-polymers | from greater than 0 wt % to about 1.0 wt % |
| DEET | from about 15 wt % to about 50 wt % |
| 2-ethylhexyl 2-cyano-3,3-diphenyl-2-propenoate | greater than 0.0 wt % to about 9.0 wt % |
| 3,3,5-trimethylcyclohexyl 2-hydroxybenzoate | greater than 0.0 wt % to about 9.0 wt % |
| butyloctyl salicylate | greater than 0 wt % to about 8.0 wt % |
| (RS)-2-ethylhexyl (2E)-3-(4-methoxyphenyl)prop-2-enoate | greater than 0.0 wt % to about 9.0 wt % |
| 2-ethylhexyl 2-hydroxybenzoate | greater than 0.0 wt % to about 9.0 wt % |
| tocopheryl acetate | greater than 0 wt % to about 2.0 wt % |
| 1-(4-methoxyphenyl)-3-(4-tert-butylphenyl)propane-1,3-dione | greater than 0.0 wt % to about 9.0 wt % |
| a mixture of potassium cetyl phosphate and hydrogenated palm glycerides | greater than 0 wt % to about 5.0 wt % |
| sodium hydroxide solution (20 wt % NaOH in water) | greater than 0 wt % to about 1.0 wt % |
| a mixture of phenoxyethanol, chlorphenesin and caprylyl glycol | greater than 0 wt % to about 3.0 wt % |
| citronella extract | greater than 0 wt % to about 1.0 wt % |
| one or more $C_{12-22}$ alkyl methacrylate polymers or co-polymers | from greater than 0 wt % to about 5.0 wt % | wherein all weight percents are based on a total weight of said composition.

16. The composition of claim 15, wherein said composition comprises components and amounts as shown below:

| Component | Amount |
| --- | --- |
| deionized water | 42.4 wt % |
| a crosslinked polyacrylate polymer | 0.15 wt % |
| propanediol | 2.0 wt % |
| disodium EDTA | 0.10 wt % |
| one or more $C_{10-30}$ alkyl acrylate polymers or co-polymers | 0.25 wt % |
| DEET | 20.0 wt % |
| 2-ethylhexyl 2-cyano-3,3-diphenyl-2-propenoate | 2.75 wt % |
| 3,3,5-trimethylcyclohexyl 2-hydroxybenzoate | 5.0 wt % |
| butyloctyl salicylate | 5.0 wt % |
| (RS)-2-ethylhexyl (2E)-3-(4-methoxyphenyl)prop-2-enoate | 7.5 wt % |
| 2-ethylhexyl 2-hydroxybenzoate | 5.0 wt % |
| tocopheryl acetate | 0.10 wt % |
| 1-(4-methoxyphenyl)-3-(4-tert-butylphenyl)propane-1,3-dione | 3.0 wt % |
| a mixture of potassium cetyl phosphate and hydrogenated palm glycerides | 3.0 wt % |
| sodium hydroxide solution (20 wt % NaOH in water) | 0.65 wt % |
| a mixture of phenoxyethanol, chlorphenesin and caprylyl glycol | 1.0 wt % |
| citronella extract | 0.01 wt % |
| one or more $C_{12-22}$ alkyl methacrylate polymers or co-polymers | 2.10 wt % | wherein all weight percents are based on a total weight of said composition.

17. A combination sunscreen and insect repellant composition comprising:
from about 15 weight percent (wt %) to about 50 wt % of diethyl toluamide (or N,N-Diethyl-3-methylbenzamide or DEET);
at least 15 wt % of one or more sunscreen components, each of said one or more sunscreen components being capable of absorbing ultraviolet light rays, said one or more sunscreen components comprising a combination of: (a) 1-(4-methoxyphenyl)-3-(4-tert-butylphenyl)propane-1,3-di one, (b) 2-ethylhexyl 2-cyano-3,3-diphenyl-2-propenoate, (c) 3,3,5-trimethylcyclohexyl 2-hydroxybenzoate, (d) (RS)-2-ethylhexyl (2E)-3-(4-methoxyphenyl)prop-2-enoate, and (e) 2-ethylhexyl 2-hydroxybenzoate;
a polymeric binder system comprising:
from greater than 0 wt % to about 1.0 wt % of one or more $C_{10-30}$ alkyl acrylate polymers or co-polymers; and
from greater than 0 wt % to about 5.0 wt % of one or more $C_{12-22}$ alkyl methacrylate polymers or co-polymers, said one or more $C_{12-22}$ alkyl methacrylate polymers or co-polymers comprising a co-polymer resulting from polymerization of: methacrylic acid, methyl methacrylate, butyl acrylate, and cetyl-eicosinyl methacrylate monomers; and
at least one co-solvent comprising butyloctyl salicylate;
wherein all weight percents are based on a total weight of said composition.

18. The composition of claim 17, further comprising: a crosslinked polyacrylate polymer in an amount ranging from greater than 0 wt % to about 2.0 wt % of said composition.

19. The composition of claim 17, wherein the $C_{10-30}$ alkyl co-polymer comprises a copolymer having the chemical structure below

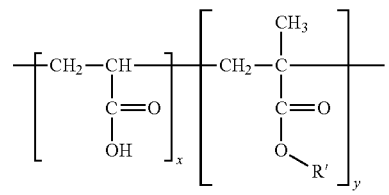

where x and y each independently comprise a number ranging from greater than 0 to 100.0, and R' represents an alkyl group having from about 10 to about 30 carbon atoms.

20. The composition of claim 17, further comprising:
said butyloctyl salicylate in an amount ranging from greater than 0 wt % to about 8.0 wt % of said composition;
a mixture of potassium cetyl phosphate and hydrogenated palm glycerides in an amount ranging from greater than 0 wt % to about 5.0 wt % of said composition;
a mixture of phenoxyethanol, chlorphenesin and caprylyl glycol in an amount ranging from greater than 0 wt % to about 3.0 wt % of said composition;
propanediol in an amount ranging from greater than 0 wt % to about 5.0 wt % of said composition;
disodium ethylenediaminetetraacetic acid (EDTA) in an amount ranging from greater than 0 wt % to about 1.0 wt % of said composition;
tocopheryl acetate in an amount ranging from greater than 0 wt % to about 2.0 wt % of said composition;
citronella extract in an amount ranging from greater than 0 wt % to about 1.0 wt % of said composition; and
deionized water in an amount ranging from greater than 0 wt % to about 60.0 wt % of said composition.

* * * * *